United States Patent
Shirai et al.

(10) Patent No.: US 11,701,024 B2
(45) Date of Patent: Jul. 18, 2023

(54) MAGNETIC RESONANCE IMAGING APPARATUS, IMAGE PROCESSOR, AND IMAGE PROCESSING METHOD

(71) Applicant: Hitachi, Ltd., Tokyo (JP)

(72) Inventors: Toru Shirai, Tokyo (JP); Suguru Yokosawa, Tokyo (JP); Hisako Nagao, Tokyo (JP); Yasuhide Yoshida, Tokyo (JP); Yasuo Kawata, Tokyo (JP); Kuniaki Harada, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 459 days.

(21) Appl. No.: 16/384,038

(22) Filed: Apr. 15, 2019

(65) Prior Publication Data
US 2020/0077893 A1 Mar. 12, 2020

(30) Foreign Application Priority Data

Sep. 7, 2018 (JP) .................. 2018-168195

(51) Int. Cl.
*A61B 5/055* (2006.01)
*A61B 5/00* (2006.01)
*G06T 7/00* (2017.01)
*G06T 15/30* (2011.01)
(Continued)

(52) U.S. Cl.
CPC ............ *A61B 5/055* (2013.01); *A61B 5/0042* (2013.01); *A61B 5/02007* (2013.01);
(Continued)

(58) Field of Classification Search
CPC ... A61B 5/0042; A61B 5/055; A61B 5/02007; G06T 7/0012; G06T 15/30; G06T 3/0068;
(Continued)

(56) References Cited

U.S. PATENT DOCUMENTS

2004/0103093 A1* 5/2004 Furuhashi ............. G06F 16/583
707/E17.02
2005/0244036 A1* 11/2005 Rusinek ................ G06T 7/0012
382/120
(Continued)

FOREIGN PATENT DOCUMENTS

JP 2005-261440 A 9/2005
JP 2015-47224 A 3/2015

OTHER PUBLICATIONS

Yang 2007 PhD Thesis Georgia Institute of Technology 127 pages (Year: 2007).*
(Continued)

*Primary Examiner* — Keith M Raymond
*Assistant Examiner* — Patrick M Mehl
(74) *Attorney, Agent, or Firm* — Foley & Lardner LLP

(57) ABSTRACT

An automatic clipping technique capable of satisfactorily extracting blood vessels to be extracted is provided. A specific tissue extraction mask image which is created by extracting a specific tissue (for example, a brain) from a three-dimensional image acquired by magnetic resonance angiography and a blood vessel extraction mask image which is created by extracting a blood vessel from an area (a blood vessel search area) which is determined using a preset landmark position and the specific tissue extraction mask image are integrated to create an integrated mask. By applying the integrated mask to the three-dimensional image, a blood vessel is clipped from the three-dimensional image.

10 Claims, 18 Drawing Sheets

(51) Int. Cl.
- *G06T 3/00* (2006.01)
- *G01R 33/563* (2006.01)
- *G01R 33/56* (2006.01)
- *A61B 5/02* (2006.01)
- *G06V 10/25* (2022.01)
- *G06V 20/64* (2022.01)

(52) U.S. Cl.
CPC ..... *G01R 33/5608* (2013.01); *G01R 33/5635* (2013.01); *G06T 3/0068* (2013.01); *G06T 7/0012* (2013.01); *G06T 15/30* (2013.01); *G06V 10/25* (2022.01); *G06V 20/64* (2022.01); *G06T 2207/10088* (2013.01); *G06T 2207/20081* (2013.01); *G06T 2207/20182* (2013.01); *G06T 2207/30016* (2013.01); *G06T 2207/30104* (2013.01)

(58) Field of Classification Search
CPC . G06T 2207/30104; G06T 2207/10088; G06T 2207/20081; G06T 2207/20182; G06T 2207/30016; G06T 2207/30101; G06T 7/11; G06K 9/46; G06K 2209/051; G06K 9/00201; G06K 9/3233; G01R 33/5635; G01R 33/5608
See application file for complete search history.

(56) References Cited

U.S. PATENT DOCUMENTS

| | | | |
|---|---|---|---|
| 2007/0206848 A1* | 9/2007 | Ohishi | G06K 9/00 382/154 |
| 2010/0296709 A1* | 11/2010 | Ostrovsky-Berman | G06T 7/11 382/128 |
| 2012/0195485 A1* | 8/2012 | Matsuba | A61B 5/0263 382/131 |
| 2016/0300351 A1* | 10/2016 | Gazit | G06T 7/11 |

OTHER PUBLICATIONS

Tamburo 2006 PhD. Thesis Engineering University of Pittsburg, 185 pages (Year: 2006).*
Yang et al. 2017 Med. Phys. 44:5859-5872 (Year: 2017).*
Kumari et al. 2010 International Conference on Recent Trends in Information, Telecommunication and Computing, 2010 (Year: 2010).*
Noorizadeh et al. 2013 Neuroscience 2013 article 317215 6 pages (Year: 2013).*
Office Action issued in corresponding Japanese Patent Application No. 2018-168195 dated Feb. 8, 2022 with English translation.

* cited by examiner

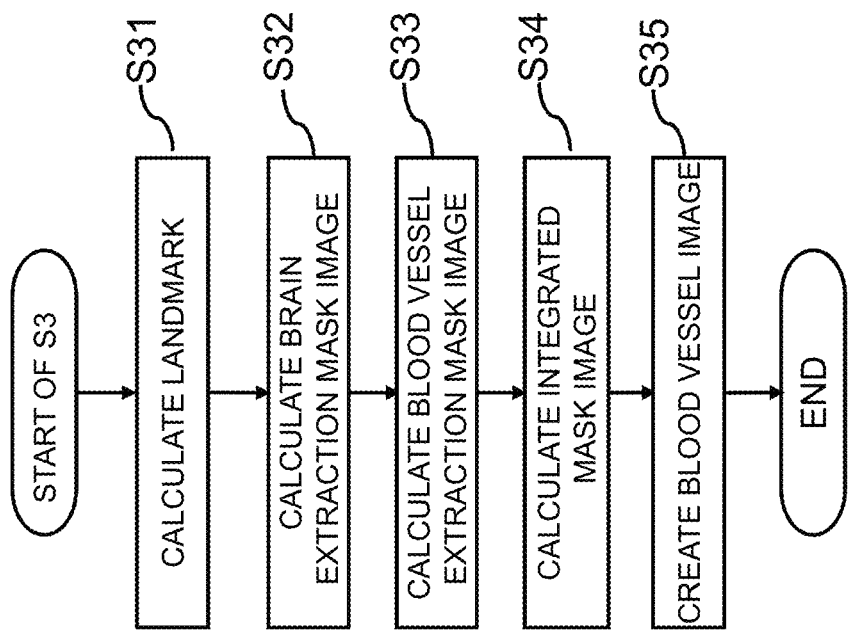

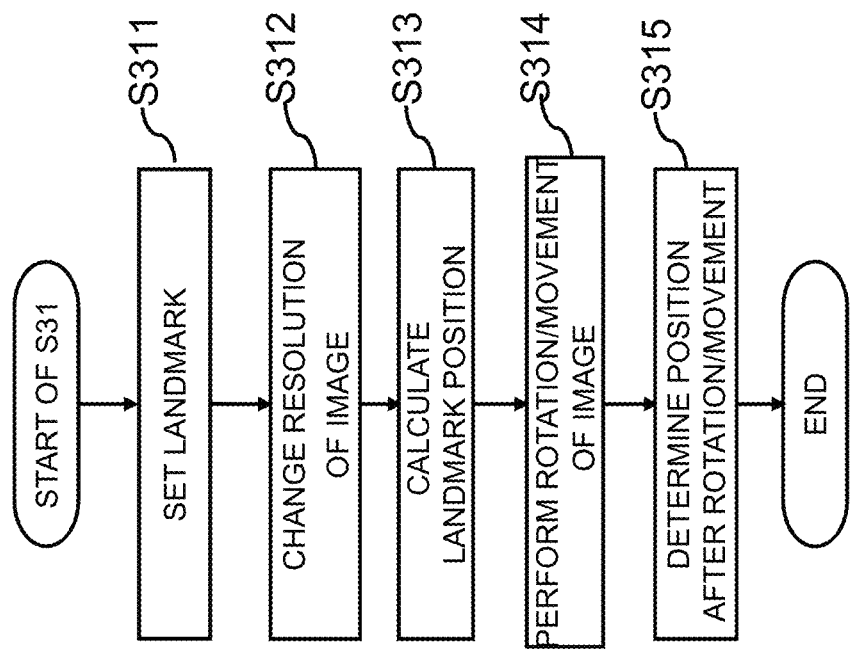

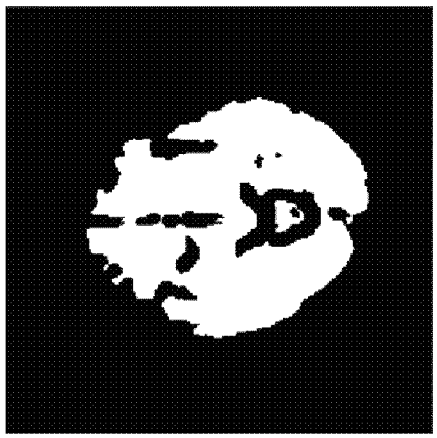
FIG.9C CONNECTED-PIXEL MAXIMUM AREA IMAGE
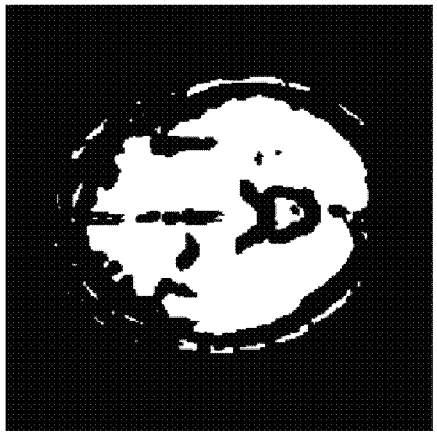
FIG.9B BINARY IMAGE
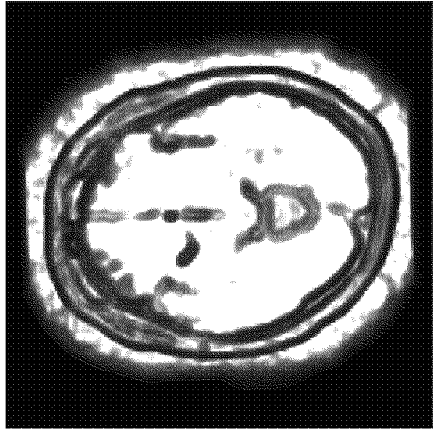
FIG.9A LOCAL SNR IMAGE
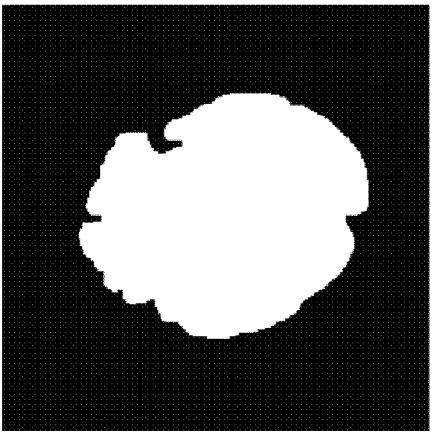
FIG.9E IMAGE AFTER FILLING
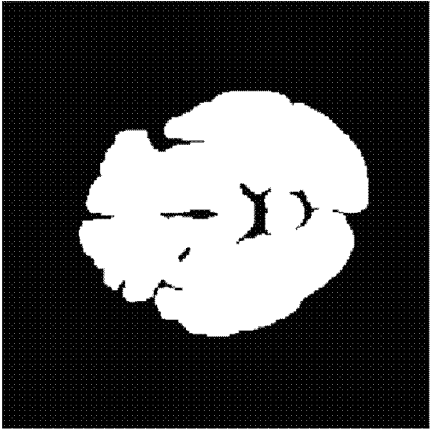
FIG.9D EXTENDED IMAGE

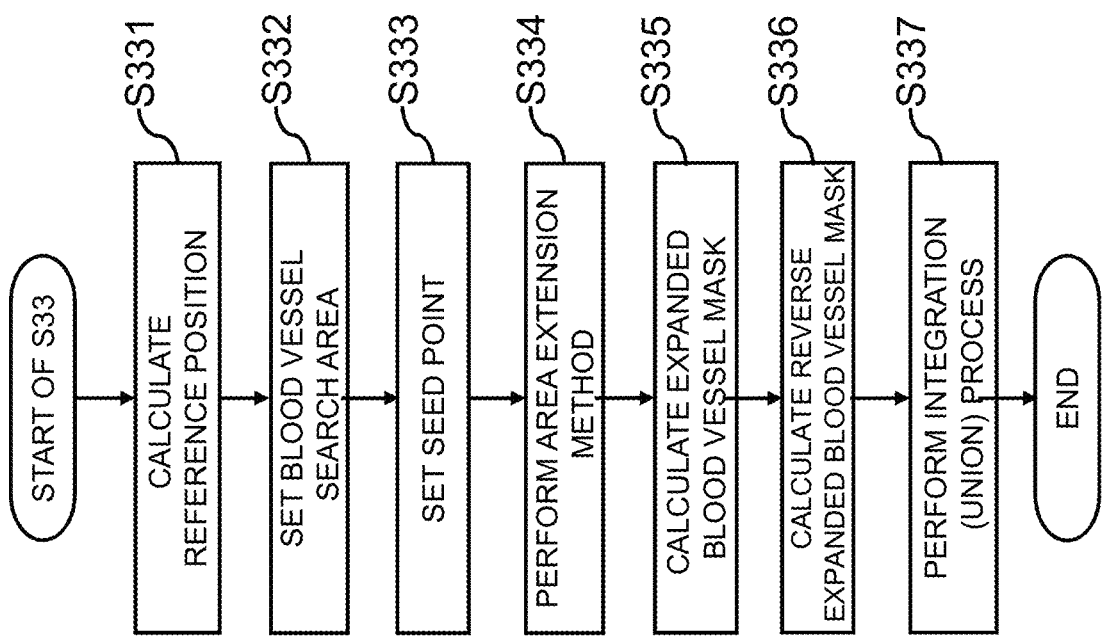

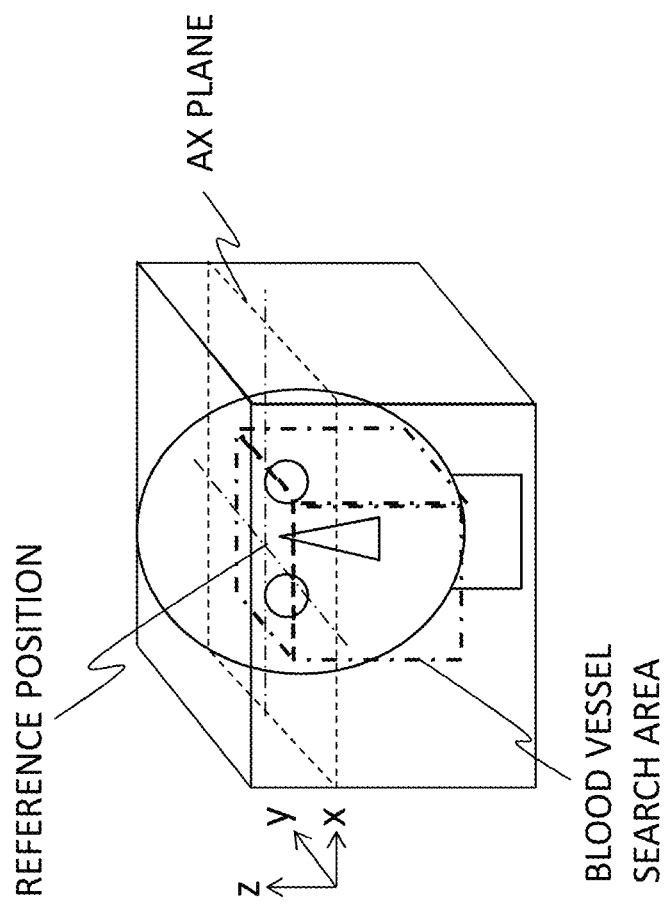

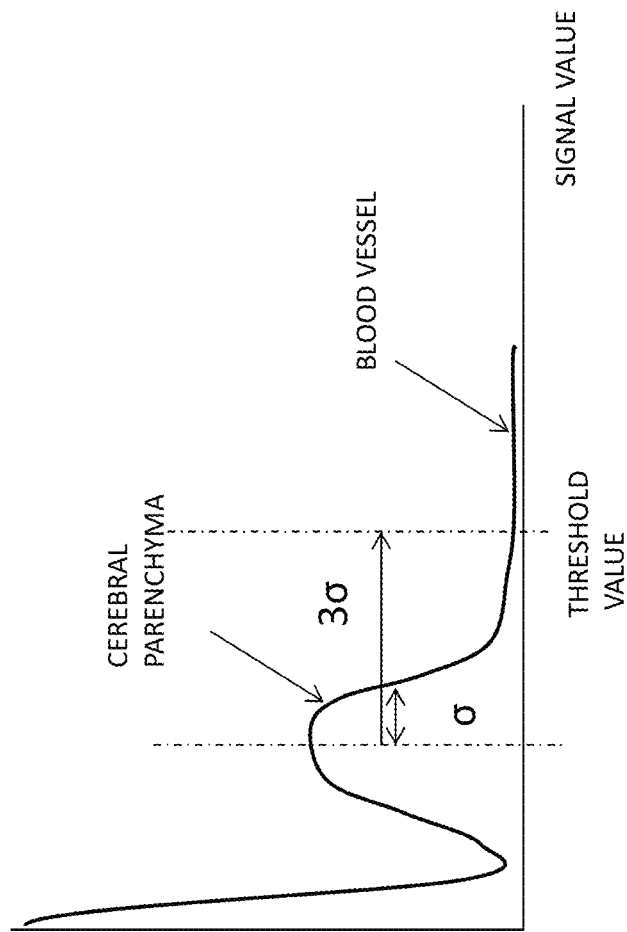

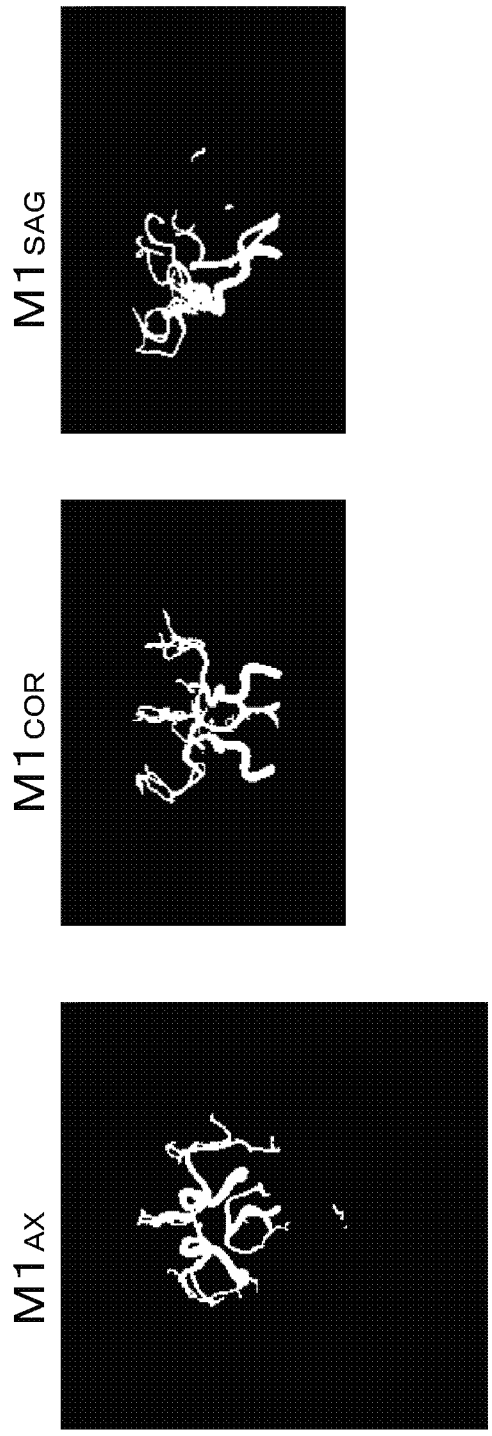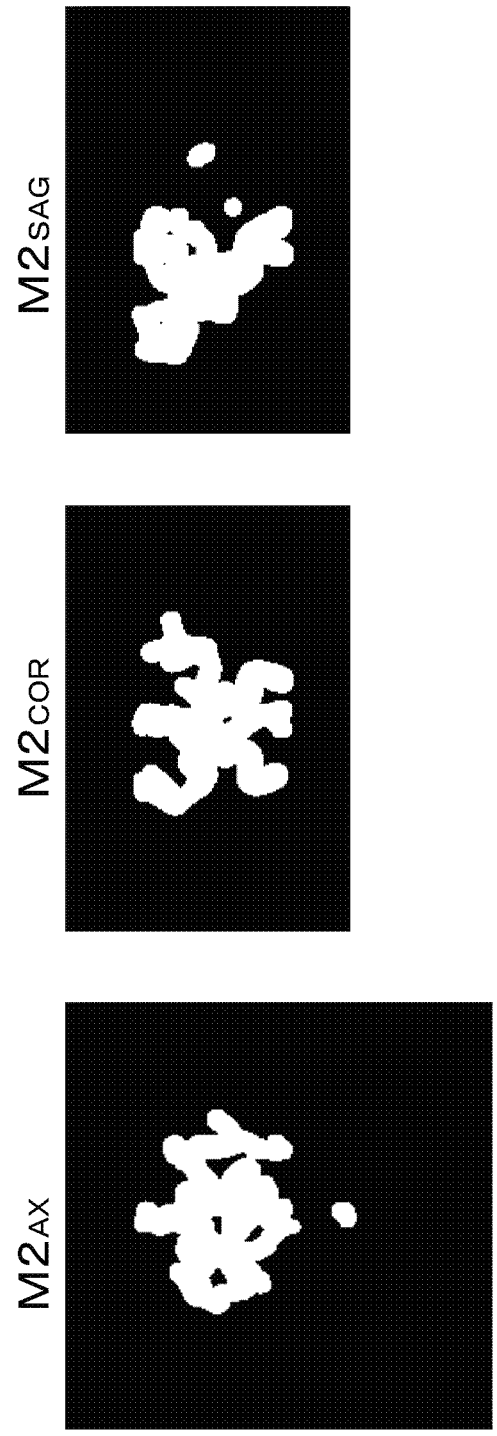
FIG.13A  BLOOD VESSEL EXTRACTION MASK AFTER AREA EXTENSION METHOD
FIG.13B  BLOOD VESSEL EXTRACTION MASK AFTER EXPANSION

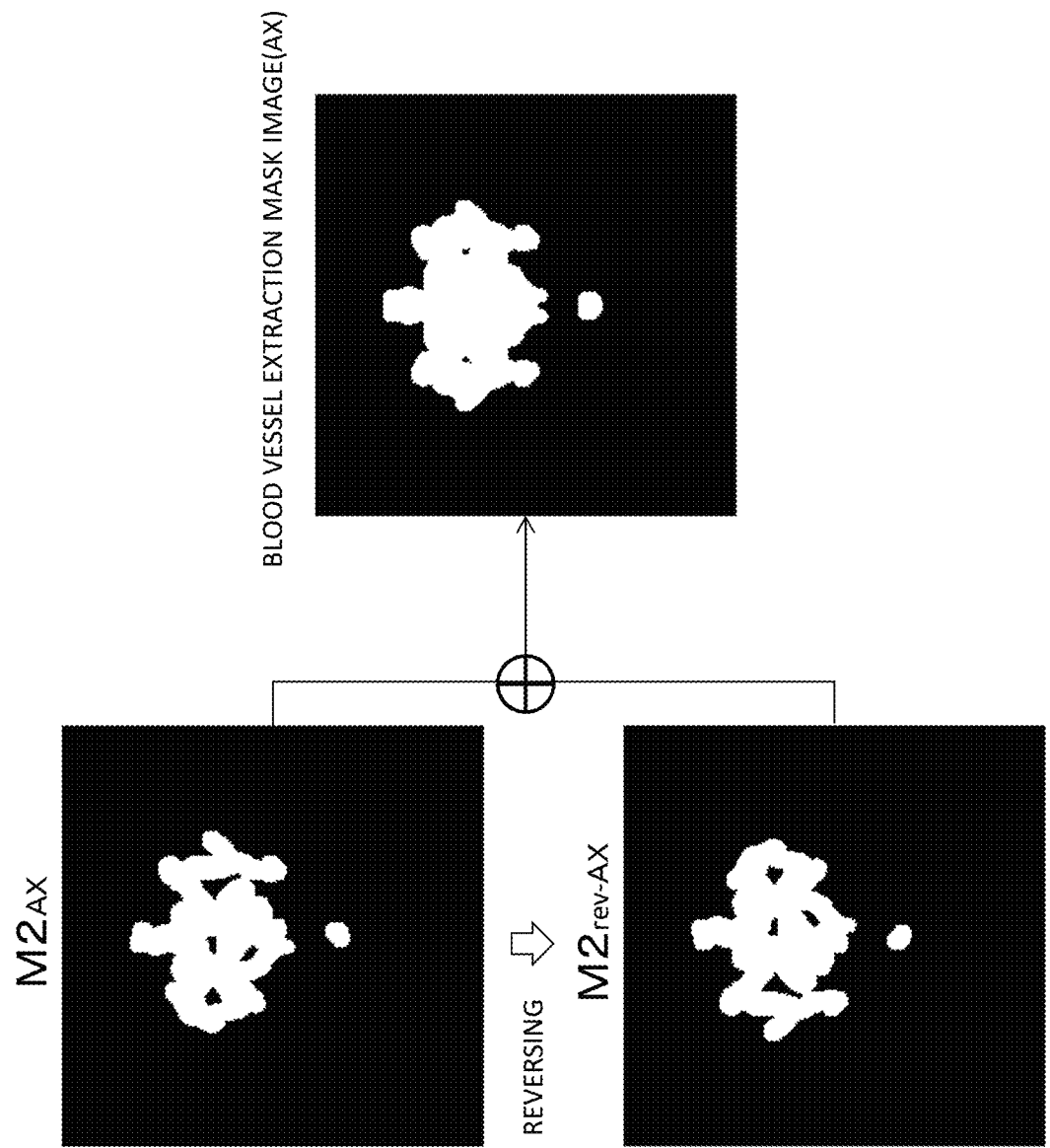

MAGNETIC RESONANCE IMAGING APPARATUS, IMAGE PROCESSOR, AND IMAGE PROCESSING METHOD

BACKGROUND OF THE INVENTION

Field of the Invention

The present invention relates to a technique of processing a blood vessel image which is acquired by a medical imaging apparatus such as a magnetic resonance imaging apparatus (hereinafter referred to as an MRI apparatus) and particularly to a technique of clipping only a blood vessel from a three-dimensional image.

Description of the Related Art

A blood vessel image is used to diagnose angiostenosis of a brain or the like. A blood vessel image can be acquired, for example, by two-dimensionally projecting a three-dimensional image including blood vessels, which is acquired using magnetic resonance angiography (MRA), using a maximum intensity projection (MIP) method. By changing the projecting directions, a blood vessel image can be seen from all angles and blood vessel abnormality or the like hidden in a thick blood vessel or the like can also be found out. Since a blood vessel image acquired by projection also includes unnecessary tissues other than a blood vessel such as subcutaneous fat or bonemarrow of a skull, an operation (a clipping operation) of removing the unnecessary tissues and clipping only blood vessels needs to be performed before an MIP image is displayed.

In the related art, clipping is manually performed and is a troublesome operation requiring labor, but automation techniques have also been proposed. For example, in an automation method described in the Patent Document listed below, clipping is performed in the following sequence. First, a mask for extracting an area (for example, a brain) of blood vessels to be observed is created using a morphological image such as a T1-weighted image. Then, a target area is extracted using a mask from a blood vessel image acquired separately from the morphological image, and a blood vessel having high signal intensity is extracted by a threshold process. Further, morphology processing is performed to extract only thick blood vessels and on the basis of the thick blood vessels, the thick blood vessels and thin blood vessels connected thereto are extracted using an area growth method.

Patent Document: JP-A-2015-47224

In the clipping technique described in JP-A-2015-47224, blood vessels are extracted using the thicknesses of blood vessels and connections thereto. However, since the thickness of a blood vessel differs depending on examinees, there is a likelihood that a thick blood vessel will not be appropriately identified and an unnecessary blood vessel will be extracted. When there is stenosis in the middle of a blood vessel, the blood vessel cannot be appropriately extracted.

In the technique described in JP-A-2015-47224, imaging for acquiring a morphological image is required separately from blood vessel imaging in order to create a mask for extracting a target area. For example, when blood vessels of a brain are observed, blood vessels below the skull as well as blood vessels in a brain area need to be extracted, but the blood vessels below the skull in an area not close to the brain area cannot be extracted with the mask for extracting the brain area.

SUMMARY OF THE INVENTION

Therefore, an objective of the invention is to provide an automatic clipping technique capable of satisfactorily extracting blood vessels to be extracted and to provide an automatic clipping technique capable of clipping blood vessels using only a blood vessel image without capturing an image other than a blood vessel image.

In order to achieve the above-mentioned objective, according to the invention, a specific tissue extraction mask image which is created by extracting a specific tissue area from a three-dimensional image acquired by magnetic resonance angiography and a blood vessel extraction mask image which is created by extracting a blood vessel from an area (a blood vessel search area) which is determined using a specific area and a preset landmark are integrated to create an integrated mask. By applying the integrated mask to the three-dimensional image, a blood vessel is clipped from the three-dimensional image.

That is, an MRI apparatus according to the invention is a magnetic resonance imaging apparatus including an imaging unit that performs imaging based on magnetic resonance angiography, collects a nuclear magnetic resonance signal from an examination object, and acquires a three-dimensional image of the examination object and an image processing unit that processes the image acquired by the imaging unit, wherein the image processing unit includes an image clipping unit that clips blood vessels in a predetermined area from the three-dimensional image and creates a three-dimensional blood vessel image. The image clipping unit includes a landmark calculating unit that calculate a position of a part serving as a landmark in the three-dimensional image acquired by the imaging unit, a first mask image creating unit that extracts a specific tissue from the three-dimensional image and creates a specific tissue extraction mask image, a second mask image creating unit that determines a blood vessel search area using the landmark position calculated by the landmark calculating unit and the specific tissue extraction mask image, extracts blood vessels included in the blood vessel search area of the three-dimensional image, and creates a blood vessel extraction mask image, and an integrated mask image creating unit that integrates the specific tissue extraction mask image and the blood vessel extraction mask image and creates an integrated mask image. Blood vessels in the predetermined area are clipped from the three-dimensional image using the integrated mask image.

The invention also provides an image processor which has a function of the image processing unit of the MRI apparatus and which is independent from the MRI apparatus.

An image processing method according to the invention is an image processing method of clipping blood vessels in a predetermined area from a three-dimensional image acquired by magnetic resonance angiography and creating a three-dimensional blood vessel image, the image processing method including: calculating a position of a part serving as a landmark in the three-dimensional image; extracting a specific tissue in the predetermined area from the three-dimensional image and creating a specific tissue extraction mask image; determining a blood vessel search area using the landmark position and the specific tissue extraction mask image, extracting blood vessels included in the blood vessel search area of the three-dimensional image, and creating a blood vessel extraction mask image; and integrating the specific tissue extraction mask image and the blood vessel extraction mask image and creating an integrated mask image. Blood vessels in the predetermined area are clipped from the three-dimensional image using the integrated mask image.

The invention also provides a program for performing the above-mentioned image processing method.

According to the invention, by integrating a specific tissue extraction mask image which is created by extracting a specific tissue in a target part and a blood vessel extraction mask image which is created separately from the specific tissue extraction mask image on the basis of a landmark included in the target part, creating an MRA mask (an integrated mask image), and using this mask image for clipping blood vessels from a three-dimensional image, it is possible to extract blood vessels in the target part without being affected by individual dependency of a blood vessel thickness. It is possible to extract a blood vessel which cannot be extracted by only connections of blood vessels due to stenosis or the like and an important blood vessel in an area close to a specific tissue. According to the invention, since only a blood vessel image is used, it is not necessary to capture other images and it is possible to prevent an imaging time from extending.

BRIEF DESCRIPTION OF THE DRAWINGS

FIG. 5 is a diagram illustrating a flow of a blood vessel clipping process in the first embodiment;

FIG. 6 is a diagram illustrating a process flow which is performed by a landmark calculating unit according to the first embodiment;

FIGS. 9A to 9E are diagrams illustrating mask images which are acquired in the process flow illustrated in FIG. 8;

FIG. 10 is a diagram illustrating a process flow which is performed by a blood vessel extraction mask image creating unit according to the first embodiment;

FIG. 11 is a diagram illustrating a process of setting a blood vessel search area in FIG. 10;

FIG. 12 is a diagram illustrating a process of setting a seed point in FIG. 10;

FIGS. 13A and 13B are diagrams illustrating mask images in the course of processing which are acquired in the process flow illustrated in FIG. 10 as MIP images of three sections, where FIG. 13A illustrates mask images acquired by an area extension process and FIG. 13B illustrates images acquired by an expansion process;

FIG. 14 is a diagram illustrating a blood vessel extraction mask image which is acquired in the process flow illustrated in FIG. 10;

DETAILED DESCRIPTION OF THE INVENTION

Hereinafter, embodiments of the invention will be described with reference to the accompanying drawings.

First Embodiment

First, the outline of an MRI apparatus according to a first embodiment will be described with reference to FIGS. 1 and 2.

Figure 1:
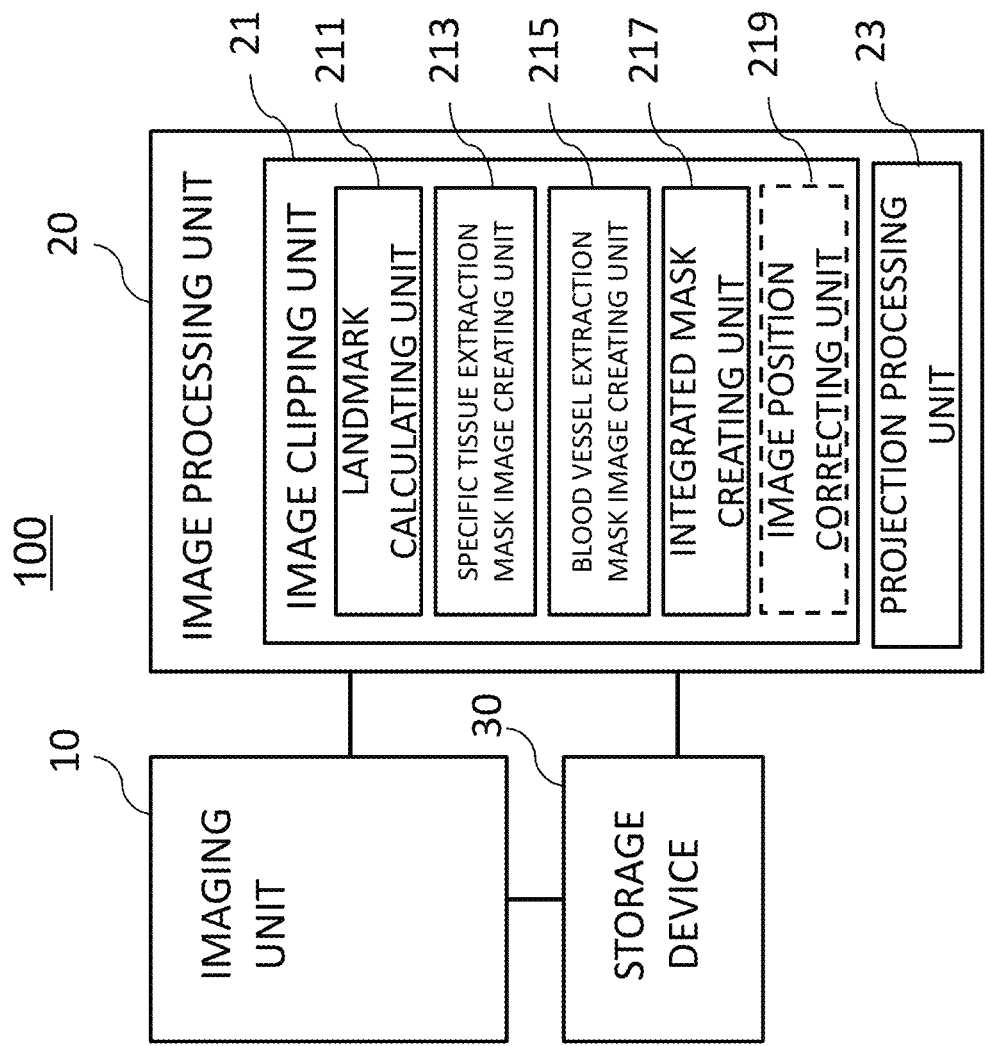
FIG. 1 is a functional block diagram illustrating details of an image processing unit according to a first embodiment.

As illustrated in FIG. 1, an MRI apparatus 100 includes an imaging unit 10 that generates nuclear magnetic resonance in nuclei of atoms constituting tissues of an examinee placed in a static magnetic field, collects nuclear magnetic resonance signals generated in response thereto, and acquires an examinee image (an MR image), an image processing unit 20 that performs various operations on the MR image acquired by the imaging unit 10, and a storage device 30 that stores process results and the like of the imaging unit 10 and the image processing unit 20.

Figure 2:
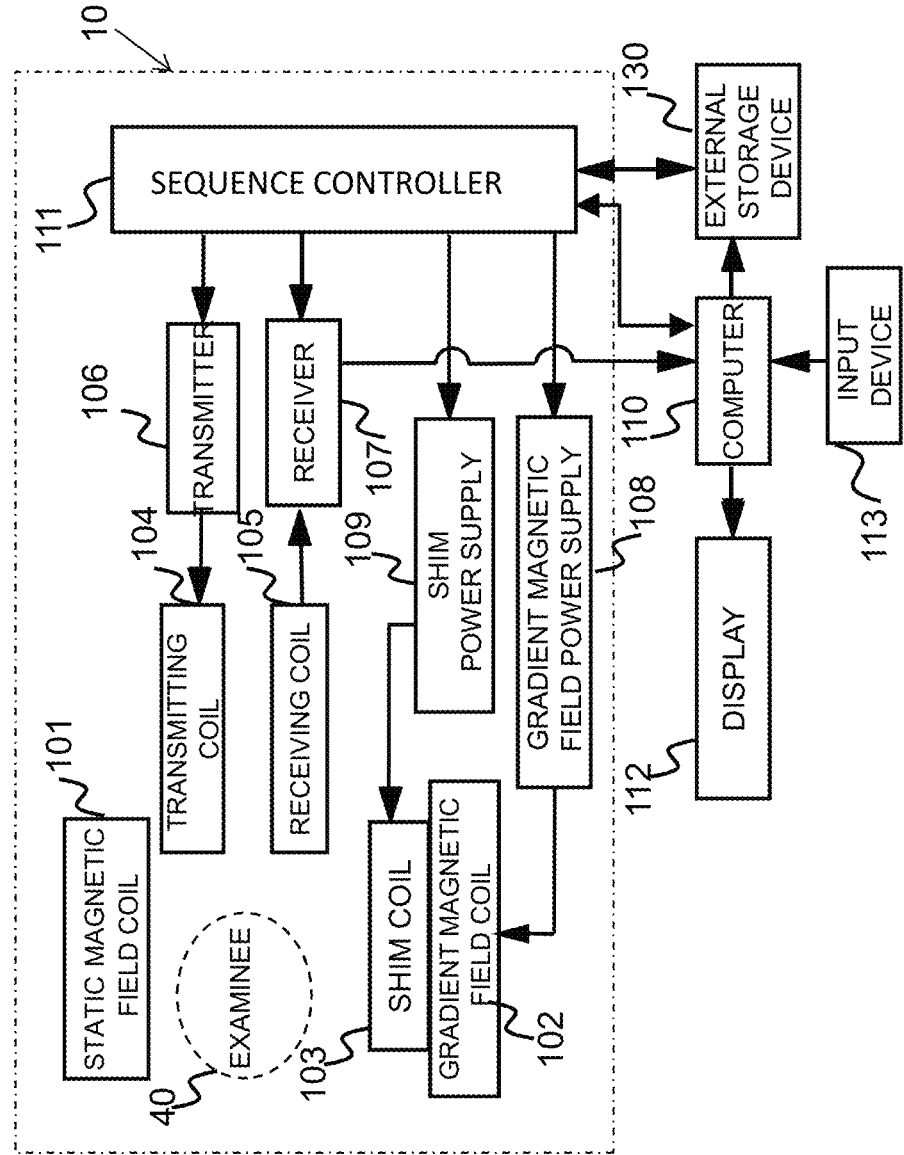
FIG. 2 is a diagram illustrating the entire outline of an MRI apparatus according to the invention.

The imaging unit 10 is the same as a general MRI apparatus and includes a static magnetic field coil 101 of super-conduction, normal-conduction, or the like or a permanent magnet that generates a static magnetic field in a space (an imaging space) in which an examinee 40 is placed, a gradient magnetic field coil 102 and a shim coil 103 that apply a magnetic field gradient to the static magnetic field, a transmitting RF coil (simply referred to as a transmitting coil) 104 that irradiates the examinee 40 with a RF pulse of a nuclear magnetic resonance frequency, a receiving RF coil (simply referred to as a receiving coil) 105 that detects a nuclear magnetic resonance signal generated from the examinee 40, and a sequence controller 111 that controls imaging in accordance with a predetermined pulse sequence as illustrated in FIG. 2.

The transmitting coil 104 is connected to a transmitter 106 that generates an RF signal, and the receiving coil 105 is connected to a receiver 107 that detects a nuclear magnetic resonance signal (an NMR signal) which is an RF signal detected by the receiving coil 105 and performs AD conversion or the like thereon.

The gradient magnetic field coil 102 includes gradient magnetic field generation coils in three axis directions perpendicular to each other, is driven by a gradient magnetic field power supply 108, applies a magnetic field gradient to the static magnetic field to give position information to the nuclear magnetic resonance signal. The shim coil 103 is driven by a shim power supply 109 and achieves uniformity of the static magnetic field which cannot be achieved by only the static magnetic field coil 101.

The sequence controller 111 controls the transmitter 106, the receiver 107, the gradient magnetic field power supply 108, and the shim power supply 109 in accordance with a preset pulse sequence and controls imaging.

The MRI apparatus 100 includes a computer 110, a display device (a display) 112, an input device 113, and an external storage device 130 that stores images or data which are process results of the computer 110 and various pulse sequences in addition to the imaging unit. The computer 110 sends imaging conditions or imaging parameters set by a user via the input device 113 or a pulse sequence to the sequence controller 111, controls the apparatus as a whole, receives an NMR signal from the receiver 107, and performs operations such as signal processing, image reconstruction, and correction. In the example illustrated in FIG. 2, the computer 110 realizes the function of the image processing unit 20 illustrated in FIG. 1. The function of the image processing unit 20 may be realized by a computer which is included in the MRI apparatus and which is separate from the computer 110 or may be an independent image processor.

As illustrated in FIG. 1, the image processing unit 20 includes an image clipping unit 21 that clips an image of a specific tissue from an MR image acquired by the imaging unit and a projection processing unit 23 that performs a projection process on the MR image or the image of the specific tissue extracted by the image clipping unit 21 and displays the resultant image on the display device. The display device that displays a projected image may be the display 112 provided to the MRI apparatus illustrated in FIG. 2 or may be another display device.

The image clipping unit 21 includes a landmark calculating unit 211, a specific tissue extraction mask image creating unit (a first mask image creating unit) 213, a blood vessel extraction mask image creating unit (a second mask image creating unit) 215, and an integrated mask image creating unit 217 as functional units for performing various computations required for clipping an image. If necessary, the image clipping unit 21 may include an image position correcting unit 219 that changes an angle or a position of a three-dimensional image which is used for clipping an image. Details of the functions will be described later.

The processes of control and operation which are performed by the computer 110 or the image processing unit 20 can be embodied in software which is incorporated into the computer 110 and are embodied by causing a CPU of the computer 110 to load a program (software) in which the order of the processes is determined and which is stored in the storage device into a memory and to execute the loaded program. Some functions may be embodied in hardware such as an application specific integrated circuit (ASIC) or a field programmable gate array (FPGA).

Figure 3:
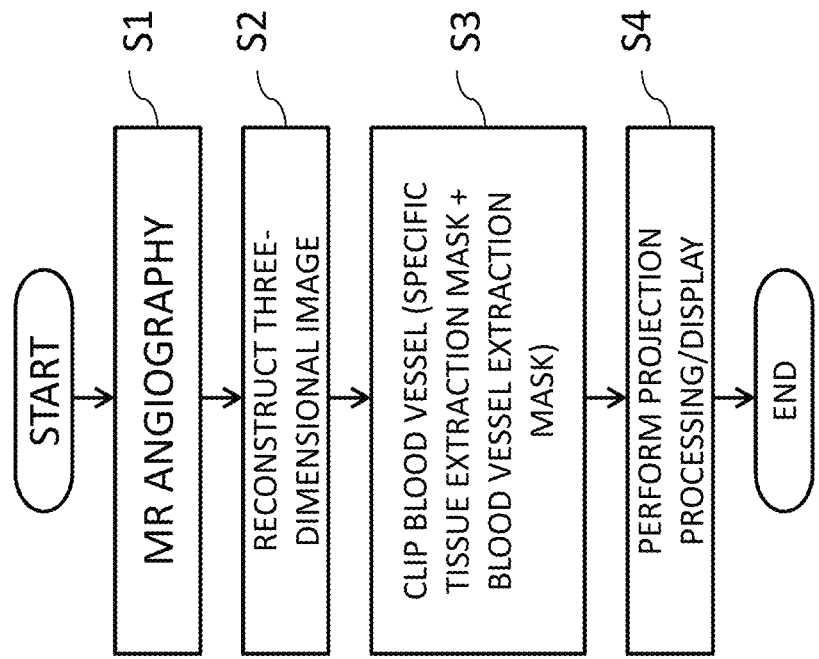
FIG. 3 is a diagram illustrating a flow from imaging of a blood vessel to displaying of a blood vessel image in the first embodiment.
Figure 4:
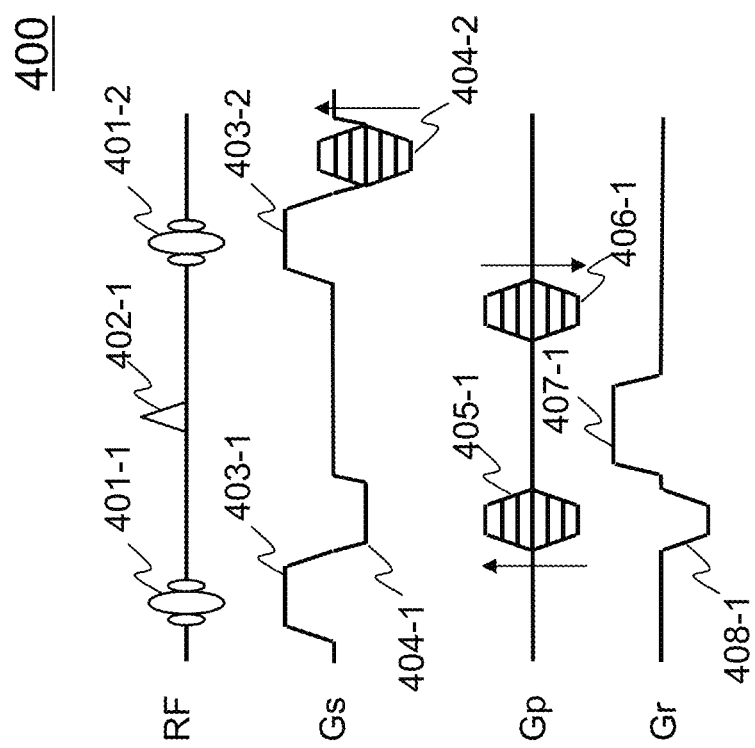
FIG. 4 is a diagram illustrating an example of a pulse sequence which is used for imaging a blood vessel.

An imaging sequence in the MRI apparatus having the above-mentioned configuration will be described below in conjunction with an example in which a blood vessel of a head is imaged. An example of the process flow is illustrated in FIG. 3. In this example, first, the imaging unit 10 performs a pulse sequence for angiography (blood vessel imaging) and acquires a blood vessel image (S1). The pulse sequence for angiography is not particularly limited, and, for example, a pulse sequence of a time of flight (TOF) illustrated in FIG. 4 is performed. In the drawing, RF represents times of application of a RF pulse 401 and acquisition of an NMR signal 402, and Gs, Gp, and Gr represent application times and magnitudes of gradient magnetic field pulses 403 to 408 in a slicing direction, a phase encoding direction, and a reading direction. Numerals subsequent to a hyphen after numerals of three digits indicate iteration and, for example, a pulse and a signal having "−1" is a pulse which is applied and a signal which is acquired in first iteration.

By causing the computer 110 to perform a reconstruction operation such as a three-dimensional Fourier transform on the NMR signals 402 collected by performing the pulse sequence for angiography, a three-dimensional image in which a blood vessel is visualized with high luminance is acquired (S2). This three-dimensional image also includes tissues other than a blood vessel. In order to remove unnecessary tissues other than a blood vessel, the image clipping unit 21 (FIG. 1) of the image processing unit 20 creates two types of masks including a specific tissue extraction mask image in which a tissue of a part including a blood vessel to be observed (a specific tissue) is extracted and a blood vessel extraction mask image in which a blood vessel is extracted and creates an image (a three-dimensional blood vessel image) in which a blood vessel part is clipped from the three-dimensional image (S3). Finally, the projection processing unit 23 performs a projection process such as a maximum intensity projection (MIP) process on the three-dimensional blood vessel image (S4). By performing the MIP at intervals of a predetermined angle in a range of 180 degrees with respect to a predetermined axis and sequentially displaying MIP images at the angles, a blood vessel can be seen in an arbitrary direction.

Specifically, as illustrated in FIG. 5, the creating of a blood vessel image (S3) includes Step S31 of causing the landmark calculating unit 211 to calculate a position of a part serving as a landmark in an MRI image in an imaging part (a head herein), Step S32 of causing the specific tissue extraction mask image creating unit 213 to calculates an image (a specific tissue extraction mask image which is referred to as a brain extraction mask image in this embodiment) which is obtained by extracting a brain part (a specific tissue) from the three-dimensional image, Step S33 of causing the blood vessel extraction mask image creating unit 215 to determine an area (a blood vessel search area) in which a blood vessel is extracted using the landmark position calculated in Step S31 and the brain extraction mask image and to calculate an image (a blood vessel extraction mask image) which is acquired by extracting a blood vessel in the area, Step S34 of causing the integrated mask image creating unit 217 to take a logic sum of the brain extraction mask image calculated in Step S32 and the blood vessel extraction mask image calculated in Step S33 and to calculate an integrated mask (integrated mask image), and Step S35 of creating a three-dimensional blood vessel image using the three-dimensional image to be processed and the integrated mask calculated in Step S34.

Details of the processes in the image clipping unit 21 will be described below.

[Calculation of Landmark: S31]

In the landmark calculating step, first, a biological tissue serving as a landmark for determining a blood vessel search area is set when a blood vessel extraction mask image which will be described later is calculated, and then a position in a three-dimensional image is calculated on the basis of anatomical features of the biological tissue. An example of the procedure of the landmark calculating step S31 is illustrated in FIG. 6.

In the example illustrated in FIG. 6, the landmark calculating unit 211 first reads user-set conditions or default-set conditions and set a predetermined biological tissue (S311). The biological tissue serving as a landmark can be appropriately selected depending on a part including the blood vessel to be diagnosed and, for example, eyeballs are set when a head blood vessel is imaged. In setting the biological tissue, eyeballs or the like may be set as a default, or a user may designate a desired biological tissue when extraction of a blood vessel in this embodiment is performed and the designation may be received by the image processing unit 20.

Then, the resolution of the three-dimensional image captured by the imaging unit 10 is converted into a low resolution (S312). By conversion into a low-resolution image, it is possible to reduce an amount of calculation for detecting eyeballs using the anatomical features. When the resolution or the FOV of the three-dimensional image differs depending on a facility in which the MRI apparatus is installed or use conditions thereof, these parameters in this process can be standardized and uniformity in accuracy of subsequent processes can be enhanced. Step S312 may be appropriately skipped depending on processing capability of the computer or the resolution may be changed.

When a landmark is set, the landmark calculating unit 211 calculates a landmark position in the three-dimensional image from the anatomical features of the set biological tissue (S313). In case of eyeballs, since it is known that an eyeball is spherical and a statistical size range of an eyeball is also known, right and left eyeballs can be detected by detecting a sphere in a predetermined size range, and the center position, an upper end in the z direction or the like of the detected sphere can be detected.

Figure 7C:
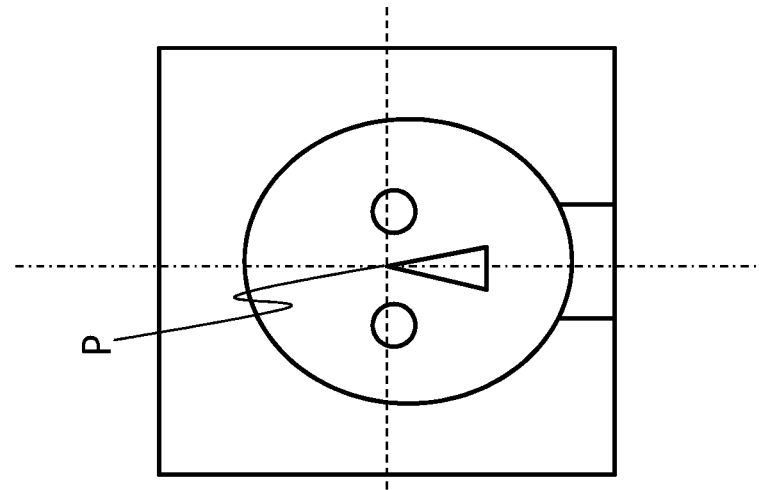
FIGS. 7A to 7C are diagrams illustrating rotation and movement of an image based on a landmark position.
Figure 7B:
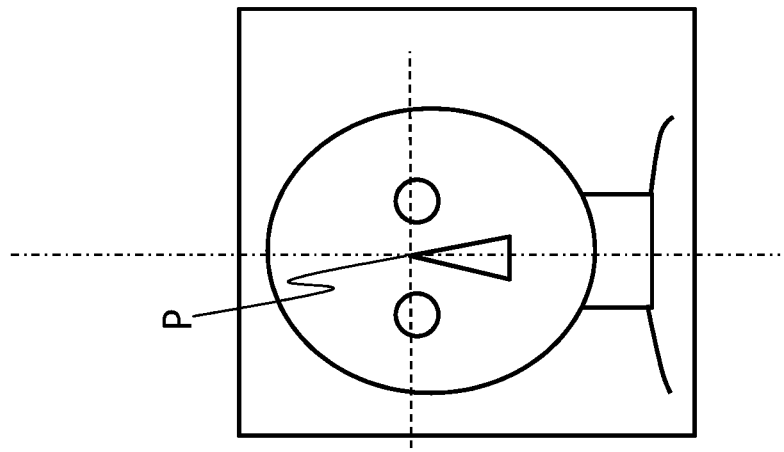
Figure 7A:
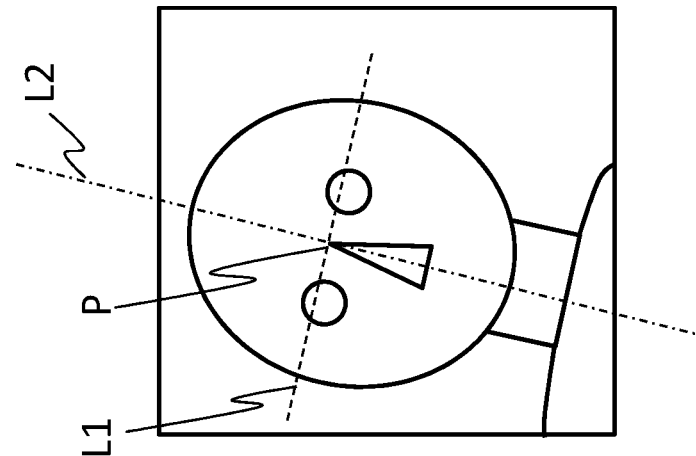

After the landmark calculating unit 211 has calculated the landmark position, the image position correcting unit 219 rotates/moves the three-dimensional image such that the landmark position is a predetermined position in the image if necessary (S314). This is illustrated in FIGS. 7A to 7C. It is ideal that an examinee is arranged in an imaging space such that an imaging region (a head) of the examinee matches the center of the static magnetic field at the time of imaging, but the imaging region may deviate slightly from the center at the time of actual imaging. In the example illustrated in FIG. 7A, a line L1 connecting the right and left eyeballs is inclined with respect to the horizontal axis of the image and a point P at which L1 crosses a center line L2 of a face deviates from the center of the image to left. In this case, the image position correcting unit 219 rotates the image such that the line L1 connecting the right and left eyeballs is parallel to the horizontal axis (the state illustrated in FIG. 7B) and moves the image in parallel such that the crossing point P is located at the center of the image (the state illustrated in FIG. 7C). The landmark calculating unit 211 sets the position after the image has been rotated/moved as the landmark position (S315). The process of rotating/moving the image may be skipped depending on the method of a blood vessel extraction mask calculating process which will be described later.

[Calculation of Brain Extraction Mask Image: S32]

The specific tissue extraction mask image creating unit 213 extracts a specific tissue, a brain herein, from the captured three-dimensional image and creates a brain extraction mask image. Some methods can be considered as a method of extracting a brain area, and a brain area is extracted using the fact that a signal from a brain tissue out of NMR signals has local uniformity (homogeneity) in this embodiment.

Figure 8:
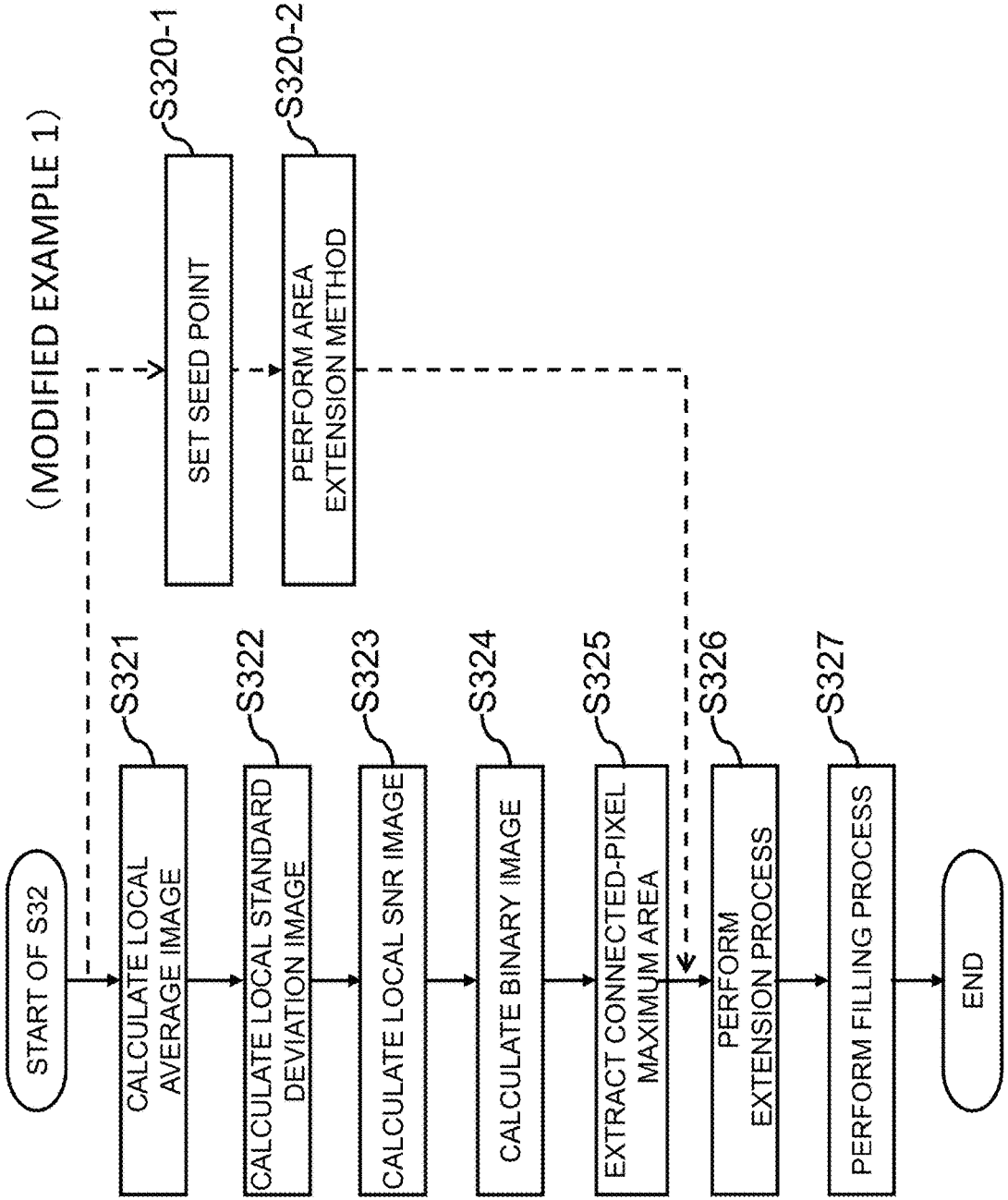
FIG. 8 is a diagram illustrating a process flow which is performed by a brain extraction mask image creating unit in the first embodiment and a modified example thereof.

The procedure of the brain extraction mask image calculating process will be described below with reference to the flow illustrated in FIG. 8.

First, a local SNR image is calculated as an image indicating local uniformity for each predetermined area (S321 to S323). Accordingly, an average and a standard deviation of pixels included in a sphere with a predetermined radius r (for example, 3 mm) are calculated for the pixels of the three-dimensional image (S321 and S323). An SNR (a signal-to-noise ratio) is calculated for each pixel using the average and the standard deviation of the pixels and a local SNR image having SNRs as pixels is calculated (S323). An SNR is proportional to signal intensity/standard deviation and the SNR is high in a uniform tissue, but signal values fluctuate in an area outside the brain such as a boundary between the brain and the skull and the SNR is low. Accordingly, in an SNR image, as illustrated in FIG. 9A, the brain area has high pixel values. In FIGS. 9A to 9E, images of an AX plane are illustrated, but the process of calculating a brain extraction mask image is a three-dimensional process.

Then, the local SNR image is binarized using a threshold value to calculate a binary image (S324). A binary image acquired by binarizing the SNR image illustrated in FIG. 9A is illustrated in FIG. 9B. In this image, a part of the brain with high signal intensity and a part of a head surface remain, and the size of the brain area is dominant. Therefore, in order to remove the head surface other than a target area, a maximum area in which pixels are connected is extracted in the binary image (S325). In extracting the maximum area, for example, neighboring pixels with a pixel value of "1" are connected using an area extension method, areas in which the pixels are connected are extracted, and an area in which the number of pixels is the maximum out of the plurality of extracted areas is set as the connected-pixel maximum area. Through this process, an image in which only the brain is extracted is acquired as illustrated in FIG. 9C.

The connected-pixel maximum area is extended by a predetermined size (S326). The predetermined size corresponds to a size of a local area when the local SNR image is calculated. Through this process, an edge part of the brain which is not included in the binary image acquired by binarizing the SNR image can be included. Thereafter, a filling process of replacing pixels in an area surrounded by the maximum area with the pixels in the maximum area is performed inside the extended maximum area (S327). Accordingly, a brain extraction mask image in which the inside of the outline of the brain is extracted is obtained. FIG. 9D illustrates an image before the filling process has been performed (the extended image) and FIG. 9E illustrates an image after the filling process has been performed. In the filling process, a recessed part surrounded by the maximum area in the edge of the brain may also be filled. Accordingly, a brain extraction mask image covering capillary blood vessels in the edge is obtained.

[Calculation of Blood Vessel Extraction Mask Image: S33]

A blood vessel extraction mask image is created by first determining a blood vessel search area using the landmark position calculated in Step S31 and the brain extraction mask calculated in Step S32 and then extracting a blood vessel in the area using the area extension method.

The procedure of the blood vessel extraction mask image calculating process will be described below with reference to the flow illustrated in FIG. 10.

First, in a three-dimensional image, a reference position for setting a blood vessel search area is calculated (S331). The reference position is set in the x and y directions (horizontal and vertical directions of the AX plan) for the z direction (a slicing direction of the AX plane). The reference position in the z direction is determined from the landmark position calculated in Step S31. Specifically, when the landmark is right and left eyeballs, the upper ends of the right and left eyeballs are set as the position in the z direction (the upper end position of the blood vessel search area), for example, as illustrated in FIG. 11. Alternatively the reference position in the z direction may be set to a position which is distant by a predetermined distance in the z direction from the upper ends of the right and left eyeballs.

The reference positions in the x and y directions are set to the position of the center of gravity of the brain extraction mask image calculated in Step S32. The center of gravity may be a center of gravity of the three-dimensional brain extraction mask image or may be the center of gravity of the AX plane at the reference position in the z direction. The xy coordinates thereof are set as the reference positions in the x direction and the y direction.

The blood vessel search range is set on the basis of the calculated reference position (S332). The blood vessel search area is set to, for example, a cylinder with a radius r1 centered on the reference position (x, y) or a square pillar with r1×2 as a length of one side, where the reference position in the z direction is the upper end thereof. The value of "r1" is, for example, a length (an experienced value) from the upper end of the eyeball to a cervical vertebra which is experientially calculated and a value corresponding to the age or sex of an examinee may be selected and set from an average database by age/sex stored in a storage device in advance.

When the blood vessel search area has been set, a blood vessel is extracted from the area using the area extension method. Accordingly, a pixel equal to or greater than a threshold value in a signal included in the blood vessel search area is set as a seed point (S333). Regarding the seed point, for example, a point equal to or greater than the threshold value in each of an AX plane, a COR plane, and a SAG plane passing through the reference position (x, y, z) is set as a seed point. The threshold value for search for a seed point can be set to a value with which a pixel value of a brain and a pixel value of a blood vessel can be clearly discriminated and is not particularly limited. For example, a pixel value which is half the maximum value in an image can be set as the threshold value for search for a seed point. Accordingly, a most probable seed point of a blood vessel can be extracted. Thereafter, consecutive blood vessel signals are extracted using the area extension method. The threshold value (an area-extension threshold value) which is used at this time can be set to, for example, a pixel value of a position at three times ($3\sigma$) the standard deviation a of peaks of the brain area in a histogram of pixel values in each plane as illustrated in FIG. 12. In the area extension method, the process of extracting a pixel satisfying the condition that the pixel value is equal to or greater than the area-extension threshold value from the pixels in the vicinity of the seed point is repeated while extending the area by resetting the extracted pixel as a seed point (S334).

A blood vessel extraction mask image M1 (a three-dimensional mask image) in which a blood vessel is clipped from the blood vessel search area is obtained through Steps S331 to S334. The blood vessel extraction mask image M1 after the area extension method has been performed is illustrated in FIG. 13A. In FIGS. 13A and 13B, for the purpose of easy understanding of images, an AX image ($M1_{AX}$), a COR image ($M1_{COR}$), and an SAG image ($M1_{SAG}$) which are acquired by performing MIP processing on the three-dimensional blood vessel extraction mask image in the z direction, the Y direction, and the x direction are illustrated.

Since a blood vessel equal to or greater than the threshold value is extracted in the area extension method, for example, a thin blood vessel of which pixel values are equal to or less than the threshold value or a blood vessel with occlusion may not be extracted. In order to add a blood vessel which cannot be extracted using the area extension method as described above to a final blood vessel extraction mask, the blood vessel extraction mask image M1 after the area extension has been performed is expanded and an expanded blood vessel extraction mask image M2 is calculated (S335). In this expansion, a process of setting an area with a predetermined radius r2 to the pixel values of the blood vessel is performed for each pixel in the extracted blood vessel. The radius "r2" is a value (an experienced value) which is experientially set in a range in which asymmetry of the right and left blood vessels can be compensated in a reverse expanded blood vessel extraction mask calculating process (S336) which will be described later and is set to about 5 mm to 6 mm. The expanded blood vessel extraction mask image M2 is illustrated in FIG. 13B. Here, M2 is illustrated as images of three sections $M2_{AX}$, $M2_{COR}$, and $M2_{SAG}$.

Then, the expanded blood vessel extraction mask image M2 is reversed laterally and a reverse expanded blood vessel extraction mask image M2rev is created (S336). This reversing process is performed to extract a blood vessel which is not extracted in extraction of a blood vessel based on a blood vessel extension method using the fact that a blood vessel running in the brain is basically symmetric in a lateral direction. For example, even when there is a blood vessel which has not been extracted due to occlusion or the like in one of right and left blood vessels, an image acquired by reversing the other blood vessel includes the corresponding blood vessel. Finally, a union of the expanded blood vessel extraction mask image M2 and the reverse expanded blood vessel extraction mask image M2rev is calculated to create an integrated blood vessel extraction mask image M (S337).

In this embodiment, as described above in the landmark calculating step S31, the three-dimensional image which is an original image for creating the brain extraction mask image and the blood vessel extraction mask image is rotated/moved such that SAG plane thereof is located at the center of the image, that is, the median plane (FIG. 6, Step S314) after the landmark position has been calculated. Accordingly, in Step S336, the mask image can be simply reversed in the lateral direction. When the rotation/movement step S314 is skipped, the median plane may be determined on the basis of the landmark position before reversing, and the expanded blood vessel mask image may be reversed with respect to the median plane. For example, when the landmark is right and left eyeballs, a sectional surface including the center of a line connecting the centers thereof and being perpendicular to the line can be determined as the median plane.

Through Steps S331 to S337, a blood vessel extraction mask image that appropriately covers the blood vessels in the blood vessel search area can be obtained. The MIP image of the AX plane of the blood vessel extraction mask image which is created in Steps S336 and S337 is illustrated in FIG. 14.

[Calculation of Integrated Mask Image: S34]

Figure 15:
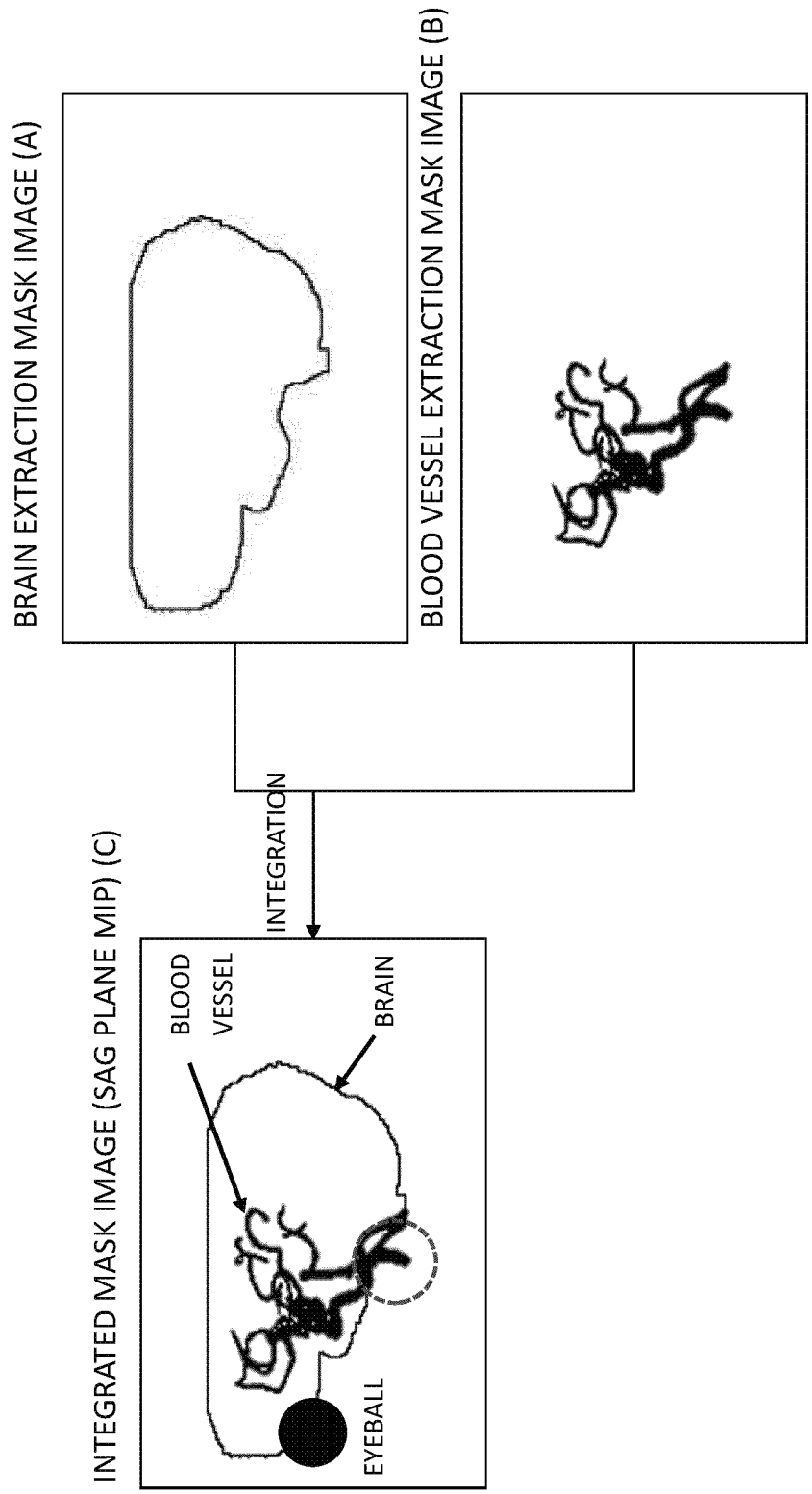
FIG. 15 is a diagram illustrating a process flow which is performed by an integrated mask image creating unit according to the first embodiment.

In this step, as illustrated in FIG. 15, a logic sum (a union) of the brain extraction mask image (A) created in Step S32 and the blood vessel extraction mask image (B) created in Step S33 is taken to create an integrated mask image (C). FIG. 15 illustrates an MIP image of the SAG plane and displays the blood vessel extraction mask image in black for the purpose of easy understanding of the integrated mask image, but both mask images are images in which pixel values in an extracted area are 1 and pixel values of the other area are 0. The integrated mask image also includes a part of a blood vessel which cannot be extracted using only the brain extraction mask image (a part surrounded with a dotted circle in the drawing), and an area extraction mask appropriately including blood vessels in the observation target area is obtained.

[Creation of Blood Vessel Image: S35]

Finally, by combining the original three-dimensional image (the MRA image acquired by the imaging unit 10) by the integrated mask image created in Step S34, a three-dimensional blood vessel image in which a blood vessel is clipped from the three-dimensional image is obtained. The projection processing unit 23 (FIG. 1) performs a projection process of the three-dimensional blood vessel image at a predetermined angle with respect to a predetermined axis and obtains an MIP image. Acquisition of an MIP image by changing the axis or the angle or continuous display of the MIP image as a moving image is the same as in the conventional processing of a blood vessel image.

In calculation of a landmark in Step S31, when the three-dimensional image is moved/rotated, a process of returning the three-dimensional image to the original angle/position may be performed after Step S34 and before the projection process is performed in Step S35. This process may be skipped similarly to Step S314.

With the image processing in the MRI apparatus according to this embodiment, by creating two different tissue extraction mask images using one MRA image, determining an area for extracting a blood vessel (a blood vessel search area) for one mask image on the basis of a landmark position calculated in advance, and creating a blood vessel extraction mask image in the area, a blood vessel in a part to be observed can be appropriately extracted regardless of its thickness thereof or presence or absence of occlusion. In creation of a brain extraction mask image, since a brain tissue is extracted using homogeneity of the brain tissue without using a segmentation technique, a brain can be extracted even from an MRA image in which contrast of cerebral parenchyma is not sufficient. Accordingly, two tissue extraction mask images can be created from one MRA image, capturing of a morphological image other than the MRA image is not required, and there is no problem with misalignment of the two mask images.

In the first embodiment, a target area is a brain or a blood vessel in the vicinity thereof, but the method according to this embodiment can also be applied to a case in which a predetermined organ such as a heart or a liver or a blood vessel in the vicinity thereof is clipped or a case in which a blood vessel in four limb regions is clipped.

In the first embodiment, a part of the image processing may be skipped or may be replaced with other means. Modified examples in which calculation of a landmark or creation of a specific tissue extraction mask is implemented using other methods will be described below as a modified example of the first embodiment.

Modified Example 1 of Landmark Calculation

In the first embodiment, a biological tissue has been detected on the basis of anatomical features in calculating a landmark, but a machine learning algorithm of learning anatomical features of biological tissues may be used to extract a biological tissue. In this modified example, Steps S311 to S313 in the flow of the landmark calculating process illustrated in FIG. 6 are replaced with Step S310 using a machine learning algorithm as illustrated in FIG. 16.

The machine learning algorithm is a learned algorithm which has learned a set of correct answer data in which an image of an eyeball which has been manually extracted is a correct answer and incorrect answer data in which an image other than an eyeball is an incorrect answer, and an algorithm programmed to detect an eyeball included in image data and to calculate the center position thereof when unknown image data is input can be used.

Figure 16:
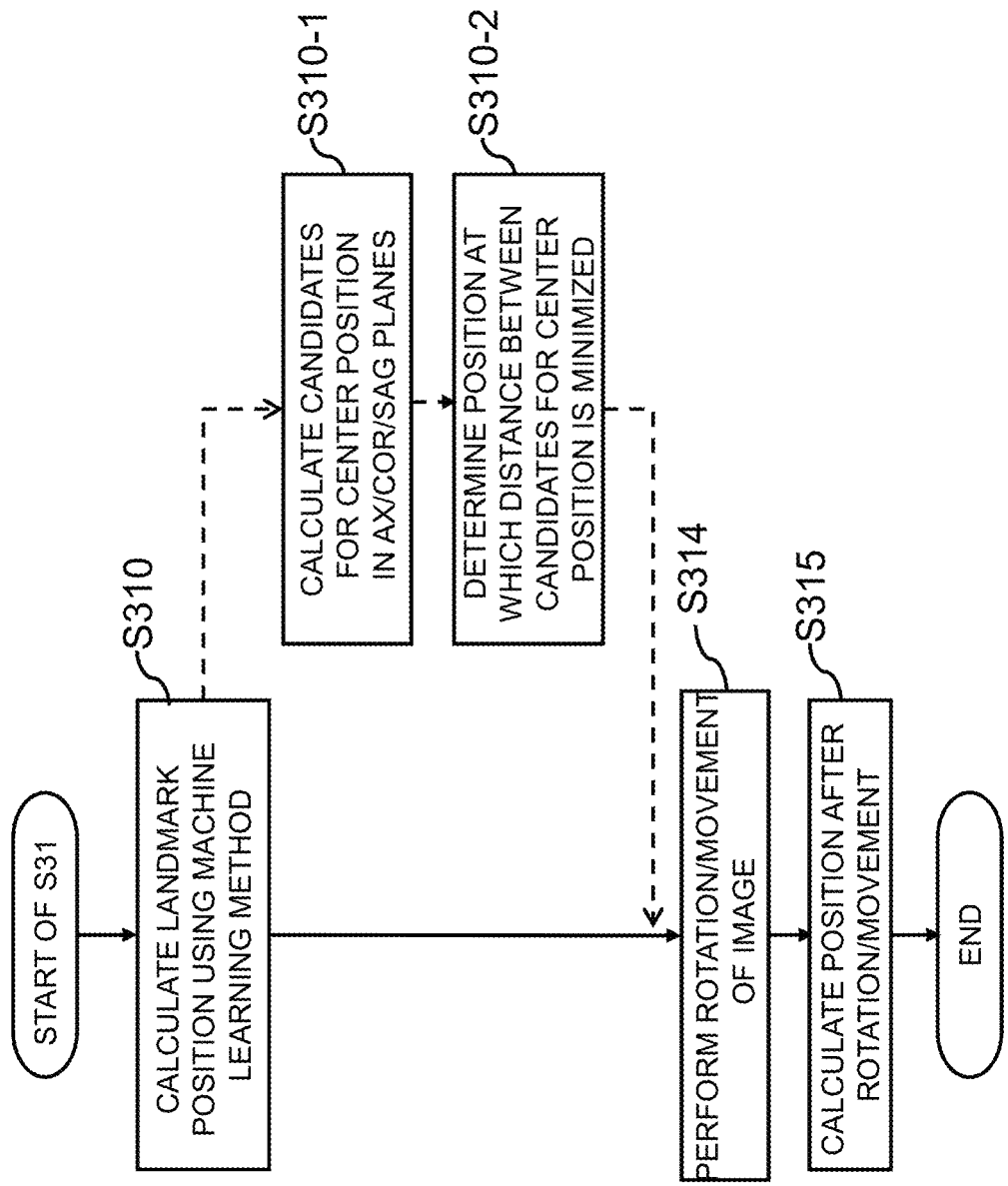
FIG. 16 is a diagram illustrating a modified example of a landmark calculating process according to the first embodiment.

A three-dimensional center position may be calculated and output directly from a three-dimensional image using the three-dimensional data as target image data of machine learning, and the center position of an eyeball in each sectional surface may be calculated using two-dimensional images of three sectional surfaces of the AX plane, the COR plane, and the SAG plane instead of the three-dimensional data (S310-1) as indicated as dotted processes (S310-1 and S310-2) in FIG. 16. The center positions calculated from the three sectional surfaces do not necessarily match each other and thus the center of gravity thereof can be set as the center position. A process of calculating a position at which the distance between the center positions of the eyeball calculated in the sectional surfaces is minimized by repeated calculation may be incorporated (S310-2). By processing two-dimensional data instead of three-dimensional data, position calculation accuracy can be enhanced even when learning is performed using a relatively small amount of learning data. In addition, by adding a process of minimizing the distance between a plurality of position candidates, accuracy can be further enhanced.

When there is a sufficient amount of learning data, deep learning (DL) using a convolutional neural network (CNN) or the like may be employed. In DL, divided image data of a three-dimensional image to be processed is input to a CNN which has learned learning data including a combination of various images and eyeball images (partial data thereof) and an image including an eyeball is extracted as output data.

When a biological tissue serving as a landmark is determined in advance, this modified example can be easily embodied by mounting a learned machine learning algorithm or a CNN for determining the landmark. Alternatively, a learned machine learning algorithm may be prepared for each of a plurality of biological tissues and the corresponding learned machine learning algorithm may be used when a user selects a biological tissue.

Modified Example 2 of Landmark Calculation

In this modified example, calculation of a landmark position is performed using a Hough transform. The Hough transform is a technique of specifying a shape of a biological tissue to be extracted using a parameter and extracting a shape satisfying the parameter form an image. When the biological tissue is an eyeball, the shape (sphere) and the radius thereof are known by experienced values and thus an eyeball can be extracted from a three-dimensional image using the parameter for specifying a sphere and a condition of the radius. Since a position at which an eyeball is located is limited, a condition such as a distance from a head top or a distance from a brain base may be added to the eyeball position and thus accuracy of eyeball extraction can be enhanced.

By using the Hough transform, an eyeball center position can be calculated in one step similarly to machine learning.

Modified Example 1 of Brain Extraction Mask
Image Calculation

In the first embodiment, an SNR image which is an image indicating homogeneity is created with attention on homogeneity of signal intensity of cerebral parenchyma, and processing such as binarization and extension is performed on the basis thereof, and a brain extraction mask image is calculated (FIG. 5: S32). In this modified example, the homogeneity of signal intensity of cerebral parenchyma is used similarly to the first embodiment, but a brain tissue is extracted using the area extension method in this modified example.

The processes in this modified example will be described below with reference back to the flow illustrated in FIG. 8 which has been referred to in the first embodiment. The process flow of the modified example in FIG. 8 is indicated by a dotted arrow.

First, a seed point is set in a three-dimensional image (S320-1). A seed point may be set to, for example, a point located a predetermined distance (a distance to a part with a high likelihood of cerebral parenchyma by experience) from the landmark position calculated in Step S31 previous to S32 or may be selected from pixels in a range of pixel values of cerebral parenchyma in the histogram illustrated in FIG. 13. In order to enhance accuracy, a plurality of seed points may be set.

Then, pixels of which a pixel value is within a predetermined range are extracted as a homogeneous tissue by the area extension method using the seed point as a start point (S320-2). The brain extraction image extracted in this way is substantially the same as the image (the image of the connected-pixel maximum area) illustrated in FIG. 9C.

Thereafter, similarly to the first embodiment, the connected-pixel maximum area image is extended by a predetermined size (S326). The size to be extended is set to, for example, about 3 mm. Then, a filling process of replacing pixels in an area surrounded by the homogenous tissue inside the extended brain extraction image and/or in an edge of the homogeneous tissue with pixels in the homogeneous tissue is performed (S327). In addition, a filling process may be performed on a recessed portion in the edge.

According to this modified example, similarly to the first embodiment, a brain extraction mask image covering capillary blood vessels in the brain edge and the like is obtained by appropriately setting the seed point.

Modified Example 2 of Brain Extraction Mask Image Calculation

In the first embodiment and the modified example (Modified Example 1 of brain extraction mask image calculation), a brain tissue is extracted from a three-dimensional image using homogeneity of signal intensity of cerebral parenchyma. On the other hand, in this modified example, a brain is extracted by removing signals of tissues other than a brain tissue, for example, subcutaneous fat or bonemarrow of the skull, from the three-dimensional image.

Figure 17:
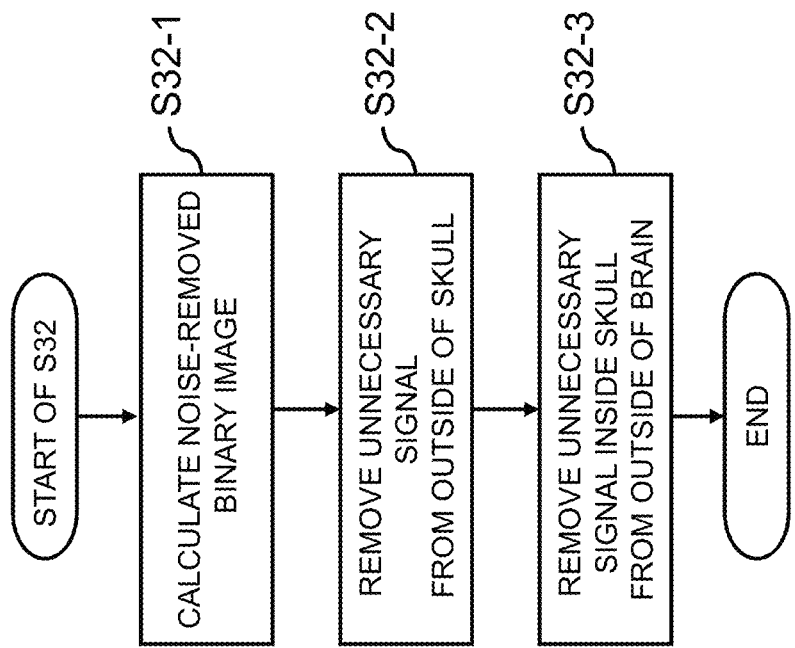
FIG. 17 is a diagram illustrating a modified example of a brain extraction mask image creating process according to the first embodiment.

The processes in this modified example will be described below with reference to the flow illustrated in FIG. 17.

First, a three-dimensional image is binarized using a threshold value and a binary image in which a value equal to or greater than the threshold value is set to 1 and a value less than the threshold value is set to 0 is calculated (S32-1). In an MRA image, signal values decrease in the order of a blood vessel (a bloodstream), subcutaneous fat, cerebral parenchyma, a skull, and noise. Accordingly, by setting the threshold value to be equal to or slightly less than a signal value of cerebral parenchyma, a binary image in which noise is removed is obtained. The skull in a binary image appears as a black area.

Then, the outside of the skull is removed from the binary image (S32-2). This process is a process of searching the pixels from the outside in the three-dimensional image and removing an area in which the pixel value is "1" and to which an area with a pixel value of "0" is adjacent in the direction toward the center. Accordingly, a subcutaneous fat signal or a bonemarrow signal outside the skull is removed.

In addition, a subcutaneous fat signal or a bonemarrow signal which is present between the skull and the brain surface is removed (S32-3). In this process, the pixels are also searched from the outside to the center in the three-dimensional image and an area in which the pixel value is "1" and to which an area with a pixel value of "0" is adjacent in the direction toward the center is removed. Accordingly, for example, even when atrophy progresses in a brain and a deep recess is formed on the brain surface, it is possible to accurately extract the brain.

As described above, according to this modified example, it is possible to create a brain extraction mask by accurately extracting a brain even when the brain has a non-standard shape by employing a method of removing unnecessary signals from the outside of an image instead of using homogeneity of signal values of a brain.

Modified Example 3 of Brain Extraction Mask Image Calculation

A brain is extracted as a specific tissue on the basis of signal values of a brain tissue in the first embodiment and Modified Example 1 and on the basis of signal values other than the brain in Modified Example 2, but a brain may be extracted by machine learning using a machine learning algorithm having learned anatomical features of a brain similarly to calculation of a landmark position (Modified Example 1) instead of using continuity or discontinuity of signal values.

In this case, since a time is required for learning of a machine learning algorithm but other operations are not required for the brain extracting process, it is possible to easily create a brain extraction mask image.

While modified examples of the first embodiment have been described above, the processes of the modified examples may be appropriately combined and employed. For example, Modified Example 1 of landmark calculation and one of Modified Examples 1 to 3 of brain extraction mask image calculation may be combined or Modified Example 2 of landmark calculation and any one of Modified Examples 1 to 3 of brain extraction mask image calculation may be combined and such a combination may be employed for Steps S31 and S32 in the first embodiment.

Second Embodiment

In the first embodiment, the function of the image processing unit 20 is embodied by the computer 110 or the like included in the MRI apparatus, but the function of the image processing unit 20 may be embodied by a workstation (a computer or the like) independent from the MRI apparatus.

Figure 18:
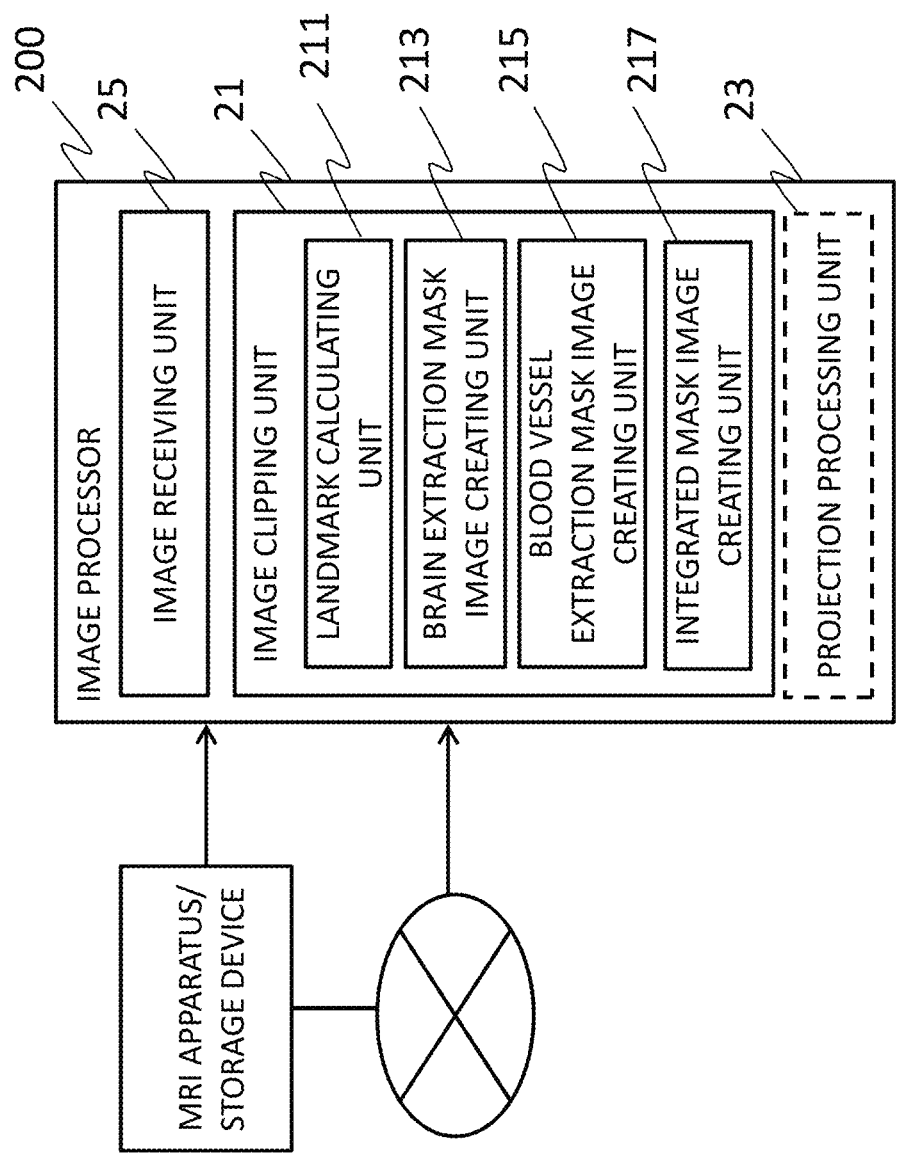
FIG. 18 is a diagram illustrating a configuration of an image processor according to a second embodiment.

A configuration in which image processing is performed by a workstation other than the MRI apparatus is illustrated in FIG. 18. In the example illustrated in FIG. 18, an image processor 200 constructed in a workstation receives an MRA image from the MRI apparatus or a storage device in which an image captured by the MRI apparatus is stored directly or via the Internet or the like and realizes the function of the image processing unit 20. The image processor 200 performs an image clipping process (the flow illustrated in FIG. 5) in accordance with an image processing program for realizing the functions of the landmark calculating unit, the specific tissue extraction mask image creating unit (the brain extraction mask image creating unit), the blood vessel extraction mask image creating unit, the integrated mask image creating unit which have been described above in the first embodiment.

That is, the image processing program is an image processing program causing a computer to perform a process of clipping blood vessels in a predetermined area from a three-dimensional image acquired by magnetic resonance angiography and creating a three-dimensional blood vessel image. The process of creating the three-dimensional blood vessel image includes a step (S31) of calculating a position of a part serving as a landmark in the three-dimensional image, a step (S32) of extracting a specific tissue in the predetermined area from the three-dimensional image and creating a specific tissue extraction mask image, a step (S33) of determining a blood vessel search area using the landmark position and the specific tissue extraction mask image, extracting blood vessels included in the blood vessel search area of the three-dimensional image, and creating a blood vessel extraction mask image, a step (S34) of integrating the specific tissue extraction mask image and the blood vessel extraction mask image and creating an integrated mask image, and a step (S35) of clipping blood vessels in the predetermined area from the three-dimensional image using the integrated mask image.

The image processing program may include a machine learning algorithm for performing at least one of the step (S31) of calculating the landmark position and the step (S32) of extracting the specific tissue. The image processing program may include an algorithm based on an area extension method for performing at least one of extraction of a specific tissue area in the step of creating the specific tissue extraction mask image and extraction of blood vessels in the step of creating the blood vessel extraction mask image.

The processing details in these steps are the same as in the processes described in the first embodiment and thus description thereof will not be repeated.

This embodiment can be appropriately modified. For example, some functions of the image processor 200, for example, the function of the projection processing unit 23 indicated by a dotted line in the drawing, may be skipped, and the image processor may perform only the function of the image clipping unit that creates an integrated mask.

What is claimed is:

1. A magnetic resonance imaging apparatus comprising:
an imager configured to perform imaging based on magnetic resonance angiography, collect a nuclear magnetic resonance signal from an examination object, and acquire a three-dimensional image of the examination object; and
at least one image processor configured to process the image acquired by the imager,
wherein the at least one processor includes an image clipping processor configured to clip only blood vessels in a predetermined area from the three-dimensional image and create a three-dimensional blood vessel image,
wherein the image clipping processor is configured to:
calculate a position of a part serving as a landmark in the three-dimensional image acquired by the imager,
correct an angle and/or a position of the three-dimensional image using the landmark position,
extract a specific tissue from the three-dimensional image and create a specific tissue extraction mask image using homogeneity of a signal intensity of the specific tissue, the specific tissue including cerebral parenchyma tissue,
determine a blood vessel search area using the landmark position and the specific tissue extraction mask image, extract blood vessels included in the blood vessel search area of the three-dimensional image, and create a blood vessel extraction mask image,
expand the blood vessel extraction mask image,
calculate a union of the expanded blood vessel extraction mask image and a reverse expanded blood vessel extraction mask image to create an integrated blood vessel extraction mask image, and
integrate the specific tissue extraction mask image and the blood vessel extraction mask image and create an integrated mask image, and
wherein blood vessels in the predetermined area are clipped from the three-dimensional image using the integrated mask image.

2. The magnetic resonance imaging apparatus according to claim 1, wherein the at least one processor is further configured to perform a projection process on the three-dimensional blood vessel image clipped, and display the resultant image on a display device.

3. An image processor configured to:
receive a three-dimensional image acquired by magnetic resonance angiography;
clip only blood vessels in a predetermined area from the three-dimensional image and create a three-dimensional blood vessel image;
calculate a position of a part serving as a landmark in the three-dimensional image received;
correct an angle and/or a position of the three-dimensional image using the landmark position, and
extract a specific tissue from the three-dimensional image and create a specific tissue extraction mask image using homogeneity of a signal intensity of the specific tissue, the specific tissue including cerebral parenchyma tissue;
determine a blood vessel search area using the landmark position calculated and the specific tissue extraction mask image, extract blood vessels included in the blood vessel search area of the three-dimensional image, and create a blood vessel extraction mask image;
expand the blood vessel extraction mask image;
calculate a union of the expanded blood vessel extraction mask image and a reverse expanded blood vessel extraction mask image to create an integrated blood vessel extraction mask image;
integrate the specific tissue extraction mask image and the blood vessel extraction mask image and create an integrated mask image; and
wherein blood vessels in the predetermined area are clipped from the three-dimensional image using the integrated mask image.

4. The image processor according to claim 3, wherein image processor is configured to create the specific tissue extraction mask image including:
set a seed point in the three-dimensional image and extract the specific tissue using an area extension method using the seed point as a start point; and
perform a filling process of replacing pixels in an area surrounded by the specific tissue with pixels of the specific tissue inside the extracted specific tissue and/or in an edge of the specific tissue.

5. A method of performing magnetic resonance imaging comprising:
performing imaging based on magnetic resonance angiography, collecting a nuclear magnetic resonance signal from an examination object, and acquiring a three-dimensional image of the examination object;

processing the image acquired;

clipping only blood vessels in a predetermined area from the three-dimensional image and creating a three-dimensional blood vessel image;

calculating a position of a part serving as a landmark in the acquired three-dimensional image;

correcting an angle and/or a position of the three-dimensional image using the landmark position;

extracting a specific tissue from the three-dimensional image and creating a specific tissue extraction mask image using homogeneity of a signal intensity of the specific tissue, the specific tissue including cerebral parenchyma tissue;

determining a blood vessel search area using the landmark position and the specific tissue extraction mask image, extracting blood vessels included in the blood vessel search area of the three-dimensional image, and creating a blood vessel extraction mask image;

expand the blood vessel extraction mask image;

calculate a union of the expanded blood vessel extraction mask image and a reverse expanded blood vessel extraction mask image to create an integrated blood vessel extraction mask image; and integrating the specific tissue extraction mask image and the blood vessel extraction mask image and creating an integrated mask image, and wherein blood vessels in the predetermined area are clipped from the three-dimensional image using the integrated mask image.

6. The method of performing magnetic resonance imaging according to claim 5, further comprising performing a projection process on the clipped three-dimensional blood vessel image, and displaying the resultant image on a display device.

7. The method of performing magnetic resonance imaging according to claim 5, further comprising creating the specific tissue extraction mask image including:

setting a seed point in the three-dimensional image and extracting the specific tissue using an area extension method using the seed point as a start point; and performing a filling process of replacing pixels in an area surrounded by the specific tissue with pixels of the specific tissue inside the extracted specific tissue and/or in an edge of the specific tissue.

8. A non-transitory computer readable medium storing a program for performing a method of performing magnetic resonance imaging, wherein when a computer executes the program, the method is performed, the method comprising:

performing imaging based on magnetic resonance angiography, collecting a nuclear magnetic resonance signal from an examination object, and acquiring a three-dimensional image of the examination object;

processing the image acquired;

clipping only blood vessels in a predetermined area from the three-dimensional image and creating a three-dimensional blood vessel image;

calculating a position of a part serving as a landmark in the acquired three-dimensional image;

correcting an angle and/or a position of the three-dimensional image using the landmark position;

extracting a specific tissue from the three-dimensional image and creating a specific tissue extraction mask image using homogeneity of a signal intensity of the specific tissue, the specific tissue including cerebral parenchyma tissue;

determining a blood vessel search area using the landmark position and the specific tissue extraction mask image, extracting blood vessels included in the blood vessel search area of the three-dimensional image, and creating a blood vessel extraction mask image;

expanding the blood vessel extraction mask image;

calculate a union of the expanded blood vessel extraction mask image and a reverse expanded blood vessel extraction mask image to create an integrated blood vessel extraction mask image; and integrating the specific tissue extraction mask image and the blood vessel extraction mask image and creating an integrated mask image, and wherein blood vessels in the predetermined area are clipped from the three-dimensional image using the integrated mask image.

9. The non-transitory computer readable medium according to claim 8, wherein the method further comprises performing a projection process on the clipped three-dimensional blood vessel image, and displaying the resultant image on a display device.

10. The non-transitory computer readable medium according to claim 8, wherein the method further comprises creating the specific tissue extraction mask image including:

setting a seed point in the three-dimensional image and extracting the specific tissue using an area extension method using the seed point as a start point; and performing a filling process of replacing pixels in an area surrounded by the specific tissue with pixels of the specific tissue inside the extracted specific tissue and/or in an edge of the specific tissue.

* * * * *